(12) United States Patent
Willmann

(10) Patent No.: US 8,618,172 B2
(45) Date of Patent: Dec. 31, 2013

(54) GALENICAL FORMULATIONS OF ORGANIC COMPOUNDS

(75) Inventor: Matthias Willmann, Basel (CH)

(73) Assignee: Novartis AG, Basel (CH)

( * ) Notice: Subject to any disclaimer, the term of this patent is extended or adjusted under 35 U.S.C. 154(b) by 388 days.

(21) Appl. No.: 12/304,244

(22) PCT Filed: Jun. 21, 2007

(86) PCT No.: PCT/EP2007/005476
§ 371 (c)(1),
(2), (4) Date: Dec. 10, 2008

(87) PCT Pub. No.: WO2007/147596
PCT Pub. Date: Dec. 27, 2007

(65) Prior Publication Data
US 2009/0203679 A1    Aug. 13, 2009

(30) Foreign Application Priority Data

Jun. 23, 2006  (GB) .................................. 0612540.5

(51) Int. Cl.
*A01N 37/18*      (2006.01)
*A61K 31/16*      (2006.01)
*A61K 31/54*      (2006.01)

(52) U.S. Cl.
USPC ..................................... 514/616; 514/223.2

(58) Field of Classification Search
USPC ........................................................ 514/616
See application file for complete search history.

(56) References Cited

U.S. PATENT DOCUMENTS

| 6,010,719 | A | 1/2000 | Remon et al. | |
| 6,099,863 | A * | 8/2000 | Gilis et al. | 424/475 |
| 2005/0182042 | A1 * | 8/2005 | Feldman et al. | 514/211.07 |
| 2005/0271720 | A1 | 12/2005 | Kolatkar et al. | 424/464 |
| 2006/0099252 | A1 * | 5/2006 | Zalit et al. | 424/464 |

FOREIGN PATENT DOCUMENTS

| EP | 0 747 050 | 6/1996 |
| WO | WO 00/32174 | 6/2000 |
| WO | WO 03/077929 | 9/2003 |
| WO | WO 03/097098 | 11/2003 |
| WO | WO 2005/089729 | 9/2005 |
| WO | WO 2005/118166 | 12/2005 |
| WO | WO 2006/041763 | 4/2006 |
| WO | WO 2006/086456 | 8/2006 |
| WO | WO 2006/116435 | 11/2006 |
| WO | WO 2007/048027 | 4/2007 |
| WO | WO 2005/077418 | 8/2008 |

OTHER PUBLICATIONS

Schmieder. Aliskiren: a clinical profile. Journal of Renin-Angiotensin-Aldosterone.*
Dietrich et al. (Pharmacokinetic Interaction of the Oral Renin Inhibitor Aliskiren With Hydrochlorothiazide in Healthy Volunteers. vol. 79, Issue 2 (Feb. 2006) American Society for Clinical Pharmacology and Therapeutics).*
"Pharmacy", 5th edition, CUI Fude, pp. 113-114, People's Medical Publishing House, Feb. 29, 2004.
Nussberger et al, Angiotensin II Suppression in Humans by the orally active Inhibitor Allskiren (SPP100); Comparison with Enalapril, Hypertension, No. 39, pp. 1-8, 2002.
Wood, et al, "Structure-based design of Aliskiren, a novel orally effective renin inhibitor", Biochemical and Biophysical Research Communications 308, pp. 698-705, 2003.
Dieterle et al, "Effect of the oral renin inhibitor Aliskiren on the pharmacokinetics and pharmacodynamics of a single dose of warfarin in healthy subjects", British Journal of Clinical Pharmacology, vol. 58. No. 4, pp. 433-436, 2004.
Stanton et al, "Blood Pressure lowering in essential hypertension with an oral renin inhibitor, Aliskiren", Hypertension, vol. 42, pp. 1137-1143, 2003.
Chueshov et al, "Industrial process of the drugs", Ministry of Health of Ukraine, vol. 2, 2002.
Desai et al, "Effect of hydroxypropyl cellulose (HPC) on dissolution rate of hydrochlorothiazide tablets", International Journal of Pharmacautics, No. 308, pp. 40-45, 2006.

* cited by examiner

*Primary Examiner* — Layla Soroush
(74) *Attorney, Agent, or Firm* — Jim Lynch

(57) ABSTRACT

The present invention relates to a solid oral dosage form comprising a therapeutically effective amount of aliskiren or a pharmaceutically acceptable salt thereof, a therapeutically effective amount of HCTZ and a hydrophilic filler selected from the group a carbohydrate or combinations thereof, e.g. sugars, sugar alcohols and starches or combinations of these.

14 Claims, No Drawings

GALENICAL FORMULATIONS OF ORGANIC COMPOUNDS

The present invention relates to solid oral dosage forms comprising an orally active renin inhibitor, aliskiren, or a pharmaceutically acceptable salt thereof, and hydrochlorothiazide (HCTZ) as the active ingredients in a suitable carrier medium. In particular, the present invention provides galenical formulations comprising the hemi-fumarate salt aliskiren in combination with hydrochlorothiazide (HCTZ). The present invention also relates to the processes for their preparation and to their use as medicaments.

In the following the term "aliskiren", if not defined specifically, is to be understood both as the free base and as a salt thereof, especially a pharmaceutically acceptable salt thereof, most preferably a hemi-fumarate thereof.

Renin released from the kidneys cleaves angiotensinogen in the circulation to form the decapeptide angiotensin I. This is in turn cleaved by angiotensin converting enzyme in the lungs, kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume. Inhibitors of the enzymatic activity of renin bring about a reduction in the formation of angiotensin I. As a result a smaller amount of angiotensin II is produced. The reduced concentration of that active peptide hormone is the direct cause of, e.g., the antihypertensive effect of renin inhibitors. Accordingly, renin inhibitors, or salts thereof, may be employed, e.g., as antihypertensives or for treating congestive heart failure. The renin inhibitor, aliskiren, in particular, a hemi-fumarate thereof, is known to be effective in the treatment of reducing blood pressure irrespective of age, sex or race and is also well tolerated. Aliskiren in form of the free base is represented by the following formula

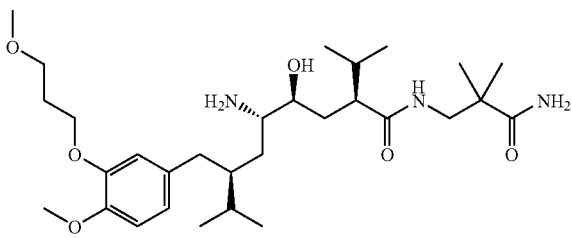

(I)

and chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide. As described above, most preferred is the hemi-fumarate salt thereof which is specifically disclosed in EP 678503 A as Example 83.

Hydrochlorothiazide is a known diuretic and the combination with Aliskiren is described, e.g. in WO02/40007.

The oral administration of such pharmaceutical agents as tablets or capsules has certain advantages over parenteral administration such as i.v. or i.m. Diseases requiring treatment with painful injectable formulations are considered to be more serious than those conditions which can be treated with oral dosage forms. However, the major advantage with oral formulations is held to be their suitability for self administration whereas parenteral formulations have to be administered in most cases by a physician or paramedical personnel.

However, aliskiren is difficult to formulate and it is not trivial to make oral formulations in the form of tablets in a reliable and robust way. In a galenical formulation comprising aliskiren, or a pharmaceutically acceptable salt thereof, a high amount is normally needed of the drug substance (DS) with properties that make the formulation of tablets difficult.

For example, aliskiren has a needle shaped crystal habit, which has a negative influence on the bulk properties of the drug substance, e.g., flow properties and bulk density. The compression behavior of the drug substance is poor, leading to weak interparticulate bonds and polymorphism changes under pressure. Aliskiren has a strong elastic component that also leads to weakening of interparticulate bonds. The high dose (up to 300 or 600 mg of the free base per tablet) makes a high drug loading necessary in order to achieve a reasonable tablet size.

The drug substance quality is very variable with effect on the processability of a tablet, e.g., particle size distribution, bulk density, flowability, wetting behavior, surface area and sticking tendency. Moreover, aliskiren is highly hygroscopic. After contact with water and removal of the water, the drug substance polymorphism changes to an amorphous state, which shows inferior stability compared to the crystalline state. The combination of these hurdles makes a standard tablet manufacturing process extremely difficult. A solid oral dosage form of Aliskiren is described in WO2005/089729.

The difficulties encountered with Aliskiren to prepare oral formulations in the form of tablets in a reliable and robust way are believed to be potentiated when using it in combination with other therapeutic agents, in particular HCTZ. Direct compression is not a feasible option for routine production of Aliskiren because of, e.g., the high hygroscopicity, the needle shaped particle structure, the poor flowability with resulting processability problems and dose uniformity problems. A roller compaction process leads to a reduction of the high bulk volume of the drug substance. Yet, the pre-compression of the drug substance during roller compaction makes a further compression into tablets with sufficient hardness and resistance to friability without a high amount of excipients extremely difficult due to the low compressibility of the drug substance. Aliskiren tends to undergo a polymorph change to a higher amorphous state under pressure, e.g. compression. Roller compaction leads to a glassy material with poor compressibility and an unsuitable release profile. Consequently, the methods developed for e.g. a formulation containing HCTZ and valsartan as disclosed in WO97/49394 involving compression methods are not applicable in the present case.

Furthermore, when using a formulation containing Aliskiren and HCTZ, the dissolution rates of both therapeutic agents must be controlled to be within an acceptable range and these dissolution rates must be balanced with a sufficient hardness and friability characteristics.

Several methods were found unsuitable to solve the object of the present invention to prepare the claimed formulation. In addition to the above-mentioned unsuitability of compression methods, also wet granulation of the drug substance of Aliskiren and HCTZ was found to be inappropriate due to a too slow drug release profile after storage. Various methods to prepare formulations containing Aliskiren in the inner phase and HCTZ in the external phase were also not successful and resulted in either poor flow characteristics or low dissolution rates.

Accordingly, a suitable and robust galenical formulation overcoming the above problems relating to the properties of aliskiren in particular when formulated together with HCTZ need to be developed.

The present invention has solved the above problems resulting in a robust formulation avoiding all the above disadvantages and in a process suitable for large-scale manufacture of solid oral dosage forms.

The present invention relates to a solid oral dosage form comprising
 a) a therapeutically effective amount of Aliskiren, or a pharmaceutically acceptable salt thereof,
 b) a therapeutically effective amount of hydrochlorothiazide (HCTZ), and
 c) a hydrophilic filler selected from a carbohydrate or combinations thereof.

It was surprisingly found that the hydrophilic filler has a positive influence on the disintegration times and thus the dissolution rates of the therapeutic agents. This was completely unexpected since it is typically the purpose of a filler to impart good flow and compression characteristics to the material. Due to these effects, the amount of disintegrant can be reduced. Although a relatively high amount of distintegrant is desirable in order to ensure high dissolution rates, this has certain disadvantages when applying an aqueous coating to the tablet core later on. Therefore, if such a relatively high amount of disintegrant can be avoided due to the use of the hydrophilic filler, the resulting oral dosage form is also more robust than before.

In a preferred embodiment of the present invention, component (a) is present in an amount ranging from 25 to 47% by weight based on the total weight of the oral dosage form.

In another preferred embodiment of the present invention component (a) is present in an amount of 26 to 46, preferably 28 to 44% by weight based on the total weight of the oral dosage form.

It is preferred that component (a) is present in an amount ranging from about 75 mg to about 600 mg of the free base per unit dosage form.

In a preferred embodiment of the present invention, component (a) is present in an amount ranging from about 75 to about 300 mg of the free base per unit dosage form, in particular 75, 150 or 300 mg.

In a further preferred embodiment of the present invention, the dosage of aliskiren is in the form of a hemi-fumarate thereof and is present in an amount of about 83, about 166, about 332 or about 663 mg per unit dosage form.

In a preferred embodiment of the present invention, component (b) is present in an amount ranging from 0.5 to 10%, such as 1 to 6%, by weight based on the total weight of the oral dosage form.

In another preferred embodiment of the present invention, component (b) is present in an amount of 1.4 to 5.5, preferably 1.5 to 1.8, 2.7 to 3.1 or 4.6 to 5.0% by weight based on the total weight of the oral dosage form.

It is preferred that component (b) is present in an amount ranging from about 6 mg to about 30 mg per unit dosage form.

In a preferred embodiment of the present invention, component (b) is present in an amount ranging from about 12.5 to about 25 mg per unit dosage form, in particular 12.5 or 25 mg.

In a preferred embodiment of the present invention, component (c) is present in an amount ranging from 3 to 30% by weight based on the total weight of the oral dosage form.

In another preferred embodiment of the present invention component (c) is present in an amount of more than 5 to 25, preferably 5.5 to 7, 10 to 13 or 18 to 21% by weight based on the total weight of the oral dosage form.

It is preferred that component (c) is present in an amount ranging from about 30 mg to about 150 mg per unit dosage form.

In a preferred embodiment of the present invention, component (c) is present in an amount ranging from about 50 to about 100 mg per unit dosage form, in particular 50 or 100 mg.

Preferred examples of the carbohydrate as the hydrophilic filler include sugars, sugar alcohols and starches or combinations of these, in particular confectioner's sugar, compressible sugar, dextrates, dextrin, dextrose, lactose, mannitol, sorbitol, sucrose, starch such as corn starch, potato starch or wheat starch.

Most preferred are lactose and starch, such as wheat starch, which can be present individually or as a mixture thereof. Preferred is a mixture such as a 2:1, 1:2 or 1:1 mixture, most preferably a 1:1 mixture.

The weight ratio of component (a) to component (b) preferably ranges from about 4:1 to about 30:1, more preferably from about 6:1 to about 24:1. Most preferably, the weight ratio is about 6:1, 12:1 or 24:1 based on the free acid. When using a salt such as the hemifumarate, the ratios will be adapted accordingly. For the following ratios, the numbers refer to component (a), thus referring to the free acid or the salt, in particular the hemifumarate.

The weight ratio of component (a) to component (c) preferably ranges from about 1:1 to about 10:1, more preferably from about 1.2:1 to about 8:1. Most preferably, the weight ratio is about 1.5-7:1, such as 1.5-1.7:1, 6.0-6.8:1 or 3.0 to 3.4:1.

The weight ratio of component (b) to component (c) preferably ranges from about 0.1:1 to about 0.6:1, more preferably from about 0.2:1 to about 0.3:1. Most preferably, the weight ratio is about 0.25:1.

The solid oral dosage forms according to the present invention show desirable drug release (DR) properties. Preferably, the DR is at least 75%, more preferably at least 80%, after 45 min. for component (a). Preferably, the DR is at least 75%, more preferably at least 80%, after 60 min. for component (b). The DR is measured by standard methods known to the person skilled in the art, see the harmonized procedure set forth in the pharmacopeias USP <711> and EP 2.9.3 and JP.

The solid oral dosage forms according to the present invention also have a low friability. Preferably the friability is not more than 0.8%, more preferably not more than 0.4%. The friability is measured by standard methods known to the person skilled in the art, see the harmonized procedure set forth in the pharmacopeias USP <1216> and EP 2.9.7 and JP.

The solid oral dosage forms according to the present invention also have a desirable disintegration property. Preferably the disintegration time is not more than 40 min, more preferably not more than 30 min, such as below 27 min. The disintegration time is measured by standard methods known to the person skilled in the art, see the harmonized procedure set forth in the pharmacopeias USP <701> and EP 2.9.1 and JP.

The solid oral dosage forms according to the present invention also have a sufficient hardness. Preferably the hardness is in arrange so as to ensure a low friability, good coatability, desirably fast disintegration times and thus high dissolution rates time. The actual values for the hardness are dependent on the size of the oral dosage form. For oral dosage forms with 75 mg of aliskiren based on the free acid, preferred ranges are between 65 to 140N, more preferably 70 to 130N, such as 73 to 125N. For oral dosage forms with 150 mg of aliskiren based on the free acid, preferred ranges are between 150 to 240N, more preferably 155 to 225N, such as 160 to 220N. For oral dosage forms with 300 mg of aliskiren based on the free acid, preferred ranges are between 160 to 270N, more preferably 175 to 260N, such as 180 to 250N. The cited hardness refers to the hardness of the core of a solid oral dosage form.

The hardness is measured by standard methods known to the person skilled in the art, using e.g. equipment from Erweka and Pharmatest.

Solid oral dosage forms according to the present invention provide for the administration of the active ingredient in a relatively small oral form of sufficient hardness and short disintegration times. Furthermore, the oral dosage forms obtained are stable both to the production process and during storage, e.g., for about 2 years in conventional packaging, e.g., sealed aluminium blister packs.

The terms "effective amount" or "therapeutically effective amount" refers to the amount of the active ingredient or agent which halts or reduces the progress of the condition being treated or which otherwise completely or partly cures or acts palliatively on the condition.

Aliskiren, or a pharmaceutically acceptable salt thereof, can, e.g., be prepared in a manner known per se, especially as described in EP 678503 A, e.g., in Example 83.

Hydrochlorothiazide is a known therapeutic agent which is useful in the treatment of hypertension.

A solid oral dosage form comprises a capsule or more preferably a tablet or a film-coated tablet.

A solid oral dosage form according to the invention comprises additives or excipients that are suitable for the preparation of the solid oral dosage form according to the present invention. Tabletting aids, commonly used in tablet formulation can be used and reference is made to the extensive literature on the subject, see in particular Fiedler's "Lexicon der Hilfstoffe", 4th Edition, ECV Aulendorf 1996, which is incorporated herein by reference. These include, but are not limited to, fillers, binders, disintegrants, lubricants, glidants, stabilising agents, fillers or diluents, surfactants, film-formers, softeners, pigments and the like.

In a preferred embodiment the solid oral dosage form according to the present invention comprises as an additive a further filler in addition to component (c).

In a preferred embodiment the solid oral dosage form according to the present invention comprises as an additive, e.g. in addition to a further filler, a disintegrant.

In a preferred embodiment the solid oral dosage form according to the present invention comprises as an additive, e.g. in addition to a further filler and a disintegrant, a lubricant.

In a preferred embodiment the solid oral dosage form according to the present invention comprises as an additive, e.g. in addition to a further filler, a disintegrant and a lubricant, a glidant.

In a preferred embodiment the solid oral dosage form according to the present invention comprises as an additive, e.g. in addition to a further filler, a disintegrant, a lubricant and a glidant, a binder.

As fillers one can particularly mention celluloses, e.g., hydroxypropyl cellulose, hydroxyethyl cellulose, hydroxypropyl methyl cellulose (HPMC) and, preferably, microcrystalline cellulose, e.g., products available under the registered trade marks AVICEL, FILTRAK, HEWETEN or PHARMACEL.

As binders for wet granulation, one can particularly mention polyvinylpyrrolidones (PVP), e.g., PVP K 30, HPMC, e.g., viscosity grades 3 or 6 cps, and polyethylene glycols (PEG), e.g., PEG 4000. A most preferred binder is PVP K 30.

As disintegrants one can particularly mention carboxymethylcellulose calcium (CMC-Ca), carboxymethylcellulose sodium (CMC-Na), crosslinked PVP (e.g. CROSPOVIDONE, POLYPLASDONE or KOLLIDON XL), alginic acid, sodium alginate and guar gum, most preferably crosslinked PVP (CROSPOVIDONE), crosslinked CMC (Ac-Di-Sol), carboxymethylstarch-Na (PIRIMOJEL and EXPLOTAB). A most preferred disintegrant is CROSPOVIDONE.

As glidants one can mention in particular colloidal silica, such as colloidal silicon dioxide, e.g., AEROSIL, magnesium (Mg) trisilicate, powdered cellulose, starch, talc and tribasic calcium phosphate or combinations of these with fillers or binders, e.g., silicified microcrystalline cellulose (PROSOLV). A most preferred glidant is colloidal silicon dioxide (e.g. AEROSIL 200) as well as talc.

As lubricants one can mention in particular Mg stearate, aluminum (Al) or Ca stearate, PEG 4000 to 8000 and talc, hydrogenated castor oil, stearic acid and salts thereof, glycerol esters, Na-stearylfumarate, hydrogenated cotton seed oil and others. A most preferred lubricant is Mg stearate.

Additives to be used as filmcoating materials comprise polymers such as HPMC, PEG, PVP, polyvinylpyrrolidone-vinyl acetate copolymer (PVP-VA), polyvinyl alcohol (PVA), and sugar as film formers. A most preferred coating material is HPMC, especially HPMC 3 cps (preferred amount 5-6 mg/cm$^2$), and mixtures thereof with further additives, e.g., those available under the registered trade mark OPADRY. Further additives comprise pigments, dies, lakes, most preferred $TiO_2$ and iron oxides, anti-tacking agents like talc and softeners like PEG 3350, 4000, 6000, 8000 or others. Most preferred additives are talc and PEG 4000.

The present invention likewise relates to a solid oral dosage form comprising a therapeutically effective amount of aliskiren, or a pharmaceutically acceptable salt thereof, as an active agent, a therapeutically effective amount of HCTZ and a hydrophilic filler selected from a carbohydrate or combinations thereof. Further additives include, but are not limited to, additional fillers, binders, disintegrants, lubricants, glidants, stabilising agents, diluents, surfactants, film formers, pigments, softeners and antitacking agents and the like. The amounts of the active ingredient and further additives are preferably those as defined above or below.

The present invention likewise relates to a solid oral dosage form comprising a therapeutically effective amount of aliskiren, or a pharmaceutically acceptable salt thereof, a therapeutically effective amount of HCTZ and a hydrophilic filler selected from a carbohydrate or combinations thereof and a disintegrant as an additive. Further additives include, but are not limited to, additional fillers, binders, lubricants, glidants, stabilising agents, diluents, surfactants, film formers, pigments, softeners and antitacking agents and the like. The amounts of the active ingredient and further additives are preferably those as defined herein above or below.

The present invention likewise relates to a solid oral dosage form comprising a therapeutically effective amount of aliskiren, or a pharmaceutically acceptable salt thereof, a therapeutically effective amount of HCTZ and a hydrophilic filler selected from a carbohydrate or combinations thereof, a disintegrant and a further filler as additives. Further additives include, but are not limited to, binders, lubricants, glidants, stabilising agents, diluents, surfactants, film formers, pigments, softeners and antitacking agents and the like. The amounts of the active ingredient and further additives are preferably those as defined herein above or below.

The present invention likewise relates to a solid oral dosage form comprising a therapeutically effective amount of aliskiren, or a pharmaceutically acceptable salt thereof, a therapeutically effective amount of HCTZ and a hydrophilic filler selected from a carbohydrate or combinations thereof, a disintegrant, a further filler and a lubricant as additives. Further additives include, but are not limited to, binders, glidants, stabilising agents, diluents, surfactants, film formers, pigments, softeners and antitacking agents and the like. The amounts of the active ingredient and further additives are preferably those as defined herein above or below.

The present invention likewise relates to a solid oral dosage form comprising a therapeutically effective amount of aliskiren, or a pharmaceutically acceptable salt thereof, a therapeutically effective amount of HCTZ and a hydrophilic filler selected from a carbohydrate or combinations thereof, a disintegrant, a further filler, a lubricant and a glidant as additives. Further additives include, but are not limited to, binders, stabilising agents, diluents, surfactants, film formers, pigments, softeners and antitacking agents and the like. The amounts of the active ingredient and further additives are preferably those as defined herein above or below.

The present invention likewise relates to a solid oral dosage form comprising a therapeutically effective amount of aliskiren, or a pharmaceutically acceptable salt thereof, a therapeutically effective amount of HCTZ and a hydrophilic filler selected from a carbohydrate or combinations thereof, a disintegrant, a further filler, a lubricant, a glidant and a binder as additives. Further additives include, but are not limited to, stabilising agents, diluents, surfactants, film formers, pigments, softeners and antitacking agents and the like. The amounts of the active ingredient and further additives are preferably those as defined herein above or below.

One or more of these additives can be selected and used by a person skilled in the art having regard to the particular desired properties of the solid oral dosage form by routine experimentation and without any undue burden.

The amount of each type of additive employed, e.g., glidant, binder, disintegrant, filler or diluent and lubricant or film coat may vary within ranges conventional in the art. Thus, for example, the amount of lubricant may vary within a range of from 0.2 to 5% by weight, in particular, for Mg stearate from 0.5 to 2.0% by weight, e.g., from 0.8 to 1.5% by weight; the amount of binder may vary within a range of from 0 to about 20% by weight, e.g., from 2 to 4% by weight; the amount of disintegrant may vary within a range of from 0 to about 20% by weight, e.g., from 8 to 13% by weight; the amount of additional filler or diluent may vary within a range of from 0 to about 80% by weight, e.g., from 20 to 35% by weight; whereas the amount of glidant may vary within a range of from 0 to about 5% by weight, e.g. from 0.4 to 2% by weight; and the amount of film coat may vary within a range of 0 to 20 mg/cm$^2$, e.g. 4 to 7 mg/cm$^2$.

It is a characteristic of the present solid oral dosage forms that they contain only a relatively small amount of additives given the high content of the active agent. This enables the production of physically small unit dosage forms. The total amount of additives in a given uncoated unit dosage may be about 70% or less by weight based on the total weight of the solid oral dosage form, more particularly about 65% or less. Preferably, the additive content is in the range of about 50 to 64% by weight, more particularly, the additive content ranges from about 55 to about 63% by weight.

A preferred amount of a further filler, especially of microcrystalline cellulose, ranges from about 20 to 35, more preferably 22 to 33, % by weight per unit dosage form. This amount of filler can contribute to a desired hardness of the oral dosage form.

A preferred amount of a binder, especially of PVP K 30, ranges from about 2 to 4, more preferably 2.1 to 3.2, % by weight per unit dosage form.

A preferred amount of a disintegrant, especially of CROSPOVIDONE, ranges from about 0 to 20, more preferably 8 to 14, most preferably 9 to 13, % by weight per unit dosage form. Due to the use of the component (c), the amount of disintegrant can be controlled advantageously so as to avoid an undesirable disintegration profile, in particular to avoid a too high amount of disintegrant that can have a negative impact on the later aqueous coating.

A preferred amount of a glidant, especially of colloidal silicon dioxide, ranges from about 0 to 5, more preferably 0.4 to 2.0, most preferably 0.6 to 1.8, % by weight per unit dosage form. In addition a further glidant, such as talc, can be present preferably in amounts of about 0 to 5, more preferably 0.3 to 2.0, most preferably 0.4 to 1.8, % by weight per unit dosage form.

A preferred amount of a lubricant, especially of Mg stearate, ranges from about 0.8 to 1.8, more preferably 1.0 to 1.5, % by weight per unit dosage form.

The amounts provided herein for the additives apply equally for the uncoated unit dosage form as well as the final coated unit dosage form.

A preferred amount of a film coat, especially of HPMC 3 cps, ranges from about 4 to 7 mg/cm$^2$ per unit dosage form.

Preferred amounts of component (a) and additives are further shown in the illustrative Examples.

The absolute amounts of each additive and the amounts relative to other additives is similarly dependent on the desired properties of the solid oral dosage form and may also be chosen by the skilled artisan by routine experimentation without undue burden. For example, the solid oral dosage form may be chosen to exhibit accelerated and/or delayed release of the active agent with or without quantitative control of the release of active agent.

Thus, where accelerated release is desired a disintegrant such as crosslinked PVP, e.g., those products available under the registered trade marks POLYPLASDONE XL or KOLLIDON CL, in particular, having a molecular weight in excess of 1,000,000, more particularly, having a particle size distribution of less than 400 microns or, preferably, less than 74 microns, or comprising reactive additives (effervescent mixtures) that effect rapid disintegration of the tablet in the presence of water, for example so-called effervescent tablets that contain an acid in solid form, typically citric acid, which acts in water on a base containing chemically combined carbon dioxide, for example sodium hydrogencarbonate or sodium carbonate, and releases carbon dioxide.

Whereas if delayed release is desired one may employ coating technology for multiparticulates (e.g. pellets, minitablets), wax matrix systems, polymer matrix tablets or polymer coatings or other technologies conventional in the art.

Quantitative control of the release of the active agent can be achieved by conventional techniques known in the art. Such dosage forms are known as oral osmotic systems (e.g. OROS), coated tablets, matrix tablets, press-coated tablets, multilayer tablets and the like.

In a solid oral dosage form preferred additives are microcrystalline cellulose, hydroxypropylcellulose, crosslinked PVP, PVP, PEG, CMC-Na or CMC-Ca, Mg stearate, Ca stearate or Al stearate, anhydrous colloidal silica, talc, titatium dioxide and iron oxide pigments. The amounts of additive employed will depend upon how much active agent is to be used. The stearate, e.g., Mg stearate is preferably employed in amounts of 0.8 to 1.8% by weight. Whereas the silica is preferably employed in an amount of from 0.4 to 2.0% by weight.

The amount of aliskiren in the form of the hemi-fumarate thereof within the total weight of the uncoated unit dosage form ranges, preferably, from about 83 to about 663 mg, most preferably, the amount of aliskiren hemi-fumarate is about 83, about 166 or about 332 mg per unit dosage form.

The weight ratio of component (a) to the binder preferably ranges from about 8:1 to about 25:1, more preferably from about 11:1 to about 15:1. Most preferably, the weight ratio is about 13.5-14:1.

The weight ratio of component (a) to the disintegrant preferably ranges from about 2:1 to about 4:1, more preferably from about 2.5:1 to about 3.7:1. Most preferably, the weight ratio is about 3.2-3.4:1.

The weight ratio of component (a) to the glidants preferably ranges from about 5:1 to about 80:1, more preferably from about 6:1 to about 40:1. Most preferably, the weight ratio is about 9-32:1.

The weight ratio of component (a) to the lubricant preferably ranges from about 20:1 to about 50:1, more preferably from about 22:1 to about 38:1. Most preferably, the weight ratio is about 24-36:1.

The weight ratio of component (b) to the binder preferably ranges from about 0.2:1 to about 5:1, more preferably from about 0.3:1 to about 3:1. Most preferably, the weight ratio is about 0.5-2:1.

The weight ratio of component (b) to the disintegrant preferably ranges from about 0.1:1 to about 1:1, more preferably from about 0.1:1 to about 0.7:1. Most preferably, the weight ratio is about 0.2-0.6:1.

The weight ratio of component (b) to the glidants preferably ranges from about 0.8:1 to about 3:1, more preferably from about 1:1 to about 2:1. Most preferably, the weight ratio is about 1.1-1.5:1.

The weight ratio of component (b) to the lubricant preferably ranges from about 1:1 to about 6:1, more preferably from about 1.1:1 to about 4:1. Most preferably, the weight ratio is about 1.2-3.8:1.

The solid oral dosage forms according to the present invention may also be in the form of film-coated tablets or dragées in which case the solid oral dosage form is provided with a coating typically a polymer like HPMC, PVP or the like, sugar, shellac or other film-coating entirely conventional in the art. Attention is drawn to the numerous known methods of coating employed in the art, e.g., spray coating in a fluidized bed, e.g., by the known methods using apparatus available from Aeromatic, Glatt, Wurster or Hüttlin, in a perforated pan coater, e.g., by the known methods using aparatus from Accela Cota, Glatt, Driam or others, or other methods conventional in the art. The additives commonly used in confectioning may be employed in such methods.

A further embodiment of the present invention is a process for the manufacture of a solid oral dosage form according to the present invention.

Thus, the present invention provides a process for the manufacture of a solid oral dosage form of the present invention comprising:
i) granulating
   a) a therapeutically effective amount of Aliskiren, or a pharmaceutically acceptable salt thereof,
   b) a therapeutically effective amount of hydrochlorothiazide (HCTZ), and
   c) a hydrophilic filler selected from the carbohydrates or a combination thereof;
   and additives with a granulation liquid;
ii) drying a resulting granulate;
iii) mixing the dried granulate with outer phase excipients;
iv) compressing a resulting mixture to form a solid oral dosage as a core tablet; and
v) optionally coating a resulting core tablet to give a film-coated tablet.

This process has been found to be the best way of manufacturing suitable aliskiren+HCTZ solid oral dosage forms, especially tablets, in contrast to other methods described before. The resulting formulation shows the following advantages:

A relatively high drug loading may easily be achieved;
The formulation of tablets with sufficient hardness, resistance to friability, disintegration time, dissolution rate etc. is possible;
The sticking tendency and poor flow of the drug substance is reduced to a minimum;
A robust manufacturing process of the DP is achieved;
Scale-up of formulation and process resulting in a reproducible DP performance is achieved; and
Sufficient stability to achieve a reasonable shelf life is achieved.

The excipients may be distributed partly in the inner (granular) phase and partly in the outer phase, which is the case in the described invention. Microcrystalline cellulose (filler) and CROSPOVI DONE (disintegrant) are preferably partly in the inner and partly in the outer phase, PVP K 30 (binder), preferably only part of the inner phase, being the binder during granulation. Colloidal silicon dioxide (glidant) and Mg stearate (lubricant) are preferably partly in the inner and partly in the outer phase. Talc (glidant) is preferably only in the inner phase.

The inner phase excipients, e.g., filler, binder and disintegrant, the hydrophilic filler and the drug substance are mixed and granulated to form the granular or inner phase. Preferably, two granular phases are obtained separately, one containing component (a), the other containing component (b). Component (c) is preferably present in the granular phase containing component (b).

The granulation of each phase preferably takes place by aqueous or organic wet granulation. Preferably the granular phase containing component (a) undergoes organic wet granulation and/or the granular phase containing component (b) undergoes aqueous wet granulation. Aqueous wet granulation means that the granulation liquid is or contains water, whereby preferably the granulation takes place in the presence of starch glue as a granulation liquid. The granulation liquid for the organic wet granulation can be ethanol, a mixture of ethanol and water, a mixture of ethanol, water and isopropanol, or a solution of PVP in the before mentioned mixtures. A preferred mixture of ethanol and water ranges from about 50/50 to about 99/1 (% w/w), most preferably it is about 94/6 (% w/w). A preferred mixture of ethanol, water and isopropanol ranges from about 45/45/5 to about 98/1/1 (% w/w/w), most preferably from about 88.5/5.5/6.0 to about 91.5/4.5/4.0 (% w/w/w). In a preferred embodiment, the granulation is effected by an ethanolic solution of the binder and additional ethanol.

The granulate is dried and preferably sieved. If the granular phase is provided as two separate granular phases, the two are preferably mixed together prior to addition of the outer phase excipients.

The outer phase containing, e.g., disintegrant, filler, glidant and lubricant, is screened to the dried granulate and mixed. The mixture is compressed into tablets (cores). The cores may optionally be coated with a film-coat.

The granulate phase is defined as the inner phase, the excipients added to the granulate are defined as the outer phase of the tabletting mixture.

The invention likewise relates to a process for the preparation of solid oral dosage forms as described herein above. Such solid oral dosage form may be produced by working up components as defined herein above in the appropriate amounts, to form unit dosage forms.

Preferably, the additives in step (i) are selected from a filler, a disintegrant, a glidant, a lubricant and a binder; and the outer phase excipients in step (iii) are selected from a filler, a disintegrant, a lubricant and a glidant.

Attention is drawn to the numerous known methods of granulating, drying and mixing employed in the art, e.g., spray granulation in a fluidized bed, wet granulation in a high-shear mixer, melt granulation, drying in a fluidized-bed dryer, mixing in a free-fall or tumble blender, compressing into tablets on a single-punch or rotary tablet press.

The manufacturing of the granulate can be performed on standard equipment suitable for aqueous or organic granulation processes. The manufacturing of the final blend and the compression of tablets can also be performed on standard equipment.

For example, step (i) may be carried out by a high-shear granulator, e.g., Collette Gral; step (i) may be conducted in a fluid-bed dryer; step (iii) may be carried out by a free-fall mixer (e.g. container blender, tumble blender); and step (iv) may be carried out using a dry compression method, e.g., a rotary tablet press.

As described above, the core tablets may then be optionally film-coated.

Due to the high hygroscopicity and water sensitivity of aliskiren with respect to changes in polymorphism, the use of water has preferably to be avoided in order to prevent the drug substance from changes in polymorphism for the above stated reasons (amorphous state, inferior chemical stability). A solution for said problem is to apply an organic film-coating process.

The film-coat preferably consists of HPMC as the polymer, iron oxide pigments, titanium dioxide as coloring agent, PEG as softener and talc as anti-tacking agent. The use of coloring agents or dyes may serve to enhance the appearance as well as to identify the compositions. Other dyes suitable for use typically include carotinoids, chlorophyll and lakes.

The film coating conditions have to assure that the tablet cores do not take up considerable amounts of moisture and that the drug substance within the tablets does not closely get into contact with water droplets. This is achieved by process parameter settings that reduce the amount of humidity which gets onto the tablet cores.

The solid oral dosage forms of the present invention are useful for lowering the blood pressure, either systolic or diastolic or both. The conditions for which the instant invention is useful include, without limitation, hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction (such as Alzheimer's) and stroke, headache and chronic heart failure.

The present invention likewise relates to a method of treating hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction, e.g., Alzheimer's, stroke, headache and chronic heart failure comprising administering to an animal, including human patient, in need of such treatment a therapeutically effective solid oral dosage form according to the present invention.

The present invention likewise relates to the use of a solid oral dosage form according to the present invention for the manufacture of a medicament for the treatment of hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction, e.g., Alzheimer's, stroke, headache and chronic heart failure.

The present invention likewise relates to a pharmaceutical composition for the treatment of hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction, e.g., Alzheimer's, stroke, headache and chronic heart failure, comprising a solid oral dosage form according to the present invention.

Ultimately, the exact dose of the active agent and the particular formulation to be administered depend on a number of factors, e.g., the condition to be treated, the desired duration of the treatment and the rate of release of the active agent. For example, the amount of the active agent required and the release rate thereof may be determined on the basis of known in vitro or in vivo techniques, determining how long a particular active agent concentration in the blood plasma remains at an acceptable level for a therapeutic effect.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way.

EXAMPLE 1

Formulations

Compositions of aliskiren 75 or 150 mg (free base) and HCTZ 12.5 or 25 mg tablets in mg/unit.

| | dosage strength [mg] | | |
|---|---|---|---|
| | Aliskiren/ HCTZ 75/12.5 | Aliskiren/ HCTZ 150/25 | Aliskiren/ HCTZ 150/12.5 |
| Aliskiren granulate | | | |
| Aliskiren hemifumarate [1] | 82.875 | 165.75 | 165.75 |
| AVICEL PH102 | 45.125 | 90.25 | 90.25 |
| PVP K30 PH | 3.00 | 6.00 | 6.00 |
| PVP-XL | 7.10 | 14.20 | 14.20 |
| PVP K30 PH in gran. liq. | 3.00 | 6.00 | 6.00 |
| Ethanol denat. with 5% Isopropanol [2] | — | — | — |
| Total Aliskiren granulate | 141.10 | 282.20 | 282.20 |
| HCTZ granulate | | | |
| Hydrochlorothiazide | 12.50 | 25.0 | 12.50 |
| Lactose monohydrate | 25.00 | 50.0 | 25.00 |
| Wheat starch | 24.50 | 49.0 | 24.50 |
| Talc | 4.15 | 8.3 | 4.15 |

-continued

Compositions of aliskiren 75 or 150 mg (free base) and HCTZ 12.5 or 25 mg tablets in mg/unit.

|  | dosage strength [mg] | | |
| --- | --- | --- | --- |
|  | Aliskiren/HCTZ 75/12.5 | Aliskiren/HCTZ 150/25 | Aliskiren/HCTZ 150/12.5 |
| Silica, colloidal anhydrous | 3.50 | 7.0 | 3.50 |
| Magnesium stearate | 0.35 | 0.7 | 0.35 |
| Water, purified [2] | — | — | — |
| Total HCTZ granulate | 70.00 | 140.00 | 70.00 |
| *External phase* | | | |
| PVP XL | 18.00 | 36.00 | 35.50 |
| AVICEL PH102 | 22.00 | 44.00 | 30.50 |
| Silica, colloidal anhydrous | 0.90 | 1.80 | 1.80 |
| Mg-Stearate | 3.00 | 6.00 | 5.00 |
| Total core | 255.00 | 510.00 | 425.00 |
| *Coat* | | | |
| Basic premix black | 0.000 | 0.000 | 0.000 |
| Basic premix red | 0.000 | 0.027 | 0.000 |
| Basic premix white | 13.000 | 17.397 | 16.000 |
| Basic premix yellow | 0.000 | 0.576 | 0.000 |
| Total coat | 13.00 | 18.00 | 16.00 |
| Total FCT | 268.00 | 528.00 | 441.00 |

[1] salt factor 1.1.05
[2] removed during processing

Compositions of aliskiren 300 mg (free base) and HCTZ 12.5 or 25 mg tablets in mg/unit

|  | dosage strength [mg] | |
| --- | --- | --- |
|  | Aliskiren/HCTZ 300/25 | Aliskiren/HCTZ 300/12.5 |
| *Aliskiren granulate* | | |
| Aliskiren hemifumarate [1] | 331.50 | 331.50 |
| AVICEL PH102 | 180.50 | 180.50 |
| PVP K30 PH | 12.00 | 12.00 |
| PVP-XL | 28.40 | 28.40 |
| PVP K30 PH in gran. liq. | 12.00 | 12.00 |
| Ethanol denat. with 5% Isopropanol [2] | — | — |
| Total Aliskiren granulate | 564.40 | 564.40 |
| *HCTZ granulate* | | |
| Hydrochlorothiazide | 25.0 | 12.50 |
| Lactose monohydrate | 50.0 | 25.00 |
| Wheat starch | 49.0 | 24.50 |
| Talc | 8.3 | 4.15 |
| Silica, colloidal anhydrous | 7.0 | 3.50 |
| Magnesium stearate | 0.7 | 0.35 |
| Water, purified [2] | — | — |
| Total HCTZ granulate | 140.00 | 70.00 |
| *External phase* | | |
| PVP XL | 71.00 | 72.00 |
| AVICEL PH102 | 61.00 | 61.00 |
| Silica, colloidal anhydrous | 3.60 | 3.60 |
| Mg-Stearat | 10.00 | 9.00 |
| Total core | 850.00 | 780.00 |
| *Coat* | | |
| Basic premix black | 0.000 | 0.078 |
| Basic premix red | 0.052 | 0.062 |
| Basic premix white | 23.868 | 25.860 |
| Basic premix yellow | 2.080 | 0.000 |
| Total coat | 26.00 | 26.00 |
| Total FCT | 876.00 | 806.00 |

[1] salt factor 1.1.05
[2] removed during processing

EXAMPLE 2

Evaluation of 150/25 mg Formulation

| parameter | 150/25 mg |
| --- | --- |
| hardness [N] | 216 (202-226) |
| thickness mean [mm] | 5.8 |
| friability [%] | 0.4 |
| Disint. time [min] | 19-21 |

EXAMPLE 3

Evaluation of 75/12.5 mg Formulation

| parameter | |
| --- | --- |
| Disint. time [min] | 75/12.5 mg |
| hardness [N] | 105 (102-108) |
| thickness mean [mm] | 3.4 |
| friability [%] | 0.6 |
| Disint. time [min] | 13-14 |

EXAMPLE 4

Evaluation of 300/25 mg Formulation

| parameter | 300/25 mg |
| --- | --- |
| hardness [N] | 213 (198-230) |
| thickness mean [mm] | 7.4 |
| friability [%] | 0.2 |
| Disint. time [min] | 20-21 |

EXAMPLE 5

Evaluation of 150/12.5 ma Formulation

| parameter | 150/12.5 mg |
| --- | --- |
| hardness [N] | 198 (184-214) |
| thickness mean [mm] | 5.7 |
| friability [%] | 0.2 |
| Disint. time [min] | 18-20 |

EXAMPLE 6

Evaluation of 300/12.5 mg Formulation

| parameter | 300/12.5 mg |
| --- | --- |
| hardness [N] | 215 (196-231) |
| thickness mean [mm] | 6.9 |
| friability [%] | 0.2 |
| Disint. time [min] | 19-20 |

EXAMPLE 7

Evaluation of 300/25 mg Formulation

| Batch | Batch |
| --- | --- |
| hardness [N] | 193 (174-215) |
| thickness mean [mm] | 7.2 |
| friability [%] | 0.2 |
| Disint. time [min] | 18-20 |

The invention claimed is:

1. A solid oral dosage form comprising
   (i) 28-44% aliskiren, or a pharmaceutically acceptable salt thereof, by weight based on the total weight of the oral dosage form;
   (ii) 1.4-5.5% hydrochlorothiazide by weight based on the total weight of the oral dosage form; and
   (iii) 5-25% carbohydrate hydrophilic filler by weight based on the total weight of the oral dosage form, wherein the carbohydrate hydrophilic filler is a mixture of wheat starch and lactose;
   (iv) 22-33% microcrystalline cellulose, by weight based on the total weight of the oral dosage form;
   (v) 9-13% crosslinked polyvinylpyrrolidone, by weight based on the total weight of the oral dosage form;
   (vi) 0.6-1.8% colloidal silicon dioxide, by weight based on the total weight of the oral dosage form;
   (vii) 0.4-1.8% talc, by weight based on the total weight of the oral dosage form;
   (viii) 1-1.5% magnesium stearate, by weight based on the total weight of the oral dosage form; and
   (ix) 2.1-3.2% polyvinylpyrrolidone, by weight based on the total weight of the oral dosage form.

2. The solid oral dosage form of claim 1 wherein aliskiren comprises about 75 to about 600 mg of the free base per unit dosage form.

3. The solid oral dosage form of claim 2 wherein aliskiren comprises about 83 mg per unit dosage form.

4. The solid oral dosage form of claim 2 wherein aliskiren comprises about 166 mg per unit dosage form.

5. The solid oral dosage form of claim 2 wherein aliskiren comprises about 332 mg per unit dosage form.

6. The solid oral dosage form of claim 1 wherein hydrochlorothiazide comprises about 12.5 to about 25 mg per unit dosage form.

7. The solid oral dosage form of claim 1 wherein the carbohydrate hydrophilic filler comprises about 30 to about 150 mg per unit dosage form.

8. The solid oral dosage form of claim 7 wherein the carbohydrate hydrophilic filler comprises about 50 to about 100 mg per unit dosage form.

9. The solid oral dosage form of claim 1 in the form of a film coated tablet.

10. The solid oral dosage form of claim 1 comprising
    (i) 82.875 mg aliskiren hemifumarate;
    (ii) 12.5 mg hydrochlorothiazide;
    (iii) 25 mg lactose and 24.5 mg wheat starch;
    (iv) 67.125 mg microcrystalline cellulose;
    (v) 25.1 mg crosslinked polyvinylpyrrolidone;
    (vi) 4.4 mg colloidal silicon dioxide;
    (vii) 4.15 mg talc;
    (viii) 3.35 mg magnesium stearate; and
    (ix) 6 mg polyvinylpyrrolidone.

11. The solid oral dosage form of claim 1 comprising
    (i) 165.75 mg aliskiren hemifumarate;
    (ii) 25 mg hydrochlorothiazide;
    (iii) 50 mg lactose and 49 mg wheat starch;
    (iv) 134.25 mg microcrystalline cellulose;
    (v) 50.2 mg crosslinked polyvinylpyrrolidone;
    (vi) 8.8 mg colloidal silicon dioxide;
    (vii) 8.3 mg talc;
    (viii) 6.7 mg magnesium stearate; and
    (ix) 12 mg polyvinylpyrrolidone.

12. The solid oral dosage form of claim 1 comprising
    (i) 165.75 mg aliskiren hemifumarate;
    (ii) 12.5 mg hydrochlorothiazide;
    (iii) 25 mg lactose and 24.5 mg wheat starch;
    (iv) 120.75 mg microcrystalline cellulose;
    (v) 49.7 mg crosslinked polyvinylpyrrolidone;
    (vi) 5.3 mg colloidal silicon dioxide;
    (vii) 4.15 mg talc;
    (viii) 5.35 mg magnesium stearate; and
    (ix) 12 mg polyvinylpyrrolidone.

13. The solid oral dosage form of claim 1 comprising
    (i) 331.5 mg aliskiren hemifumarate;
    (ii) 25 mg hydrochlorothiazide;
    (iii) 50 mg lactose and 49 mg wheat starch;
    (iv) 241.5 mg microcrystalline cellulose;
    (v) 99.4 mg crosslinked polyvinylpyrrolidone;
    (vi) 10.6 mg colloidal silicon dioxide;
    (vii) 8.3 mg talc;
    (viii) 10.7 mg magnesium stearate; and
    (ix) 24 mg polyvinylpyrrolidone.

14. The solid oral dosage form of claim 1 comprising
    (i) 331.5 mg aliskiren hemifumarate;
    (ii) 12.5 mg hydrochlorothiazide;
    (iii) 25 mg lactose and 24.5 mg wheat starch;
    (iv) 241.5 mg microcrystalline cellulose;
    (v) 100.4 mg crosslinked polyvinylpyrrolidone;
    (vi) 7.1 mg colloidal silicon dioxide;
    (vii) 4.15 mg talc;
    (viii) 9.35 mg magnesium stearate; and
    (ix) 24 mg polyvinylpyrrolidone.

\* \* \* \* \*

UNITED STATES PATENT AND TRADEMARK OFFICE
CERTIFICATE OF CORRECTION

PATENT NO. : 8,618,172 B2  
APPLICATION NO. : 12/304244  
DATED : December 31, 2013  
INVENTOR(S) : Willmann Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this
Fifth Day of May, 2015

Michelle K. Lee
*Director of the United States Patent and Trademark Office*